US012808947B2

(12) United States Patent
Kang et al.

(10) Patent No.: US 12,808,947 B2
(45) Date of Patent: Nov. 24, 2026

(54) METHOD FOR DETECTING LEAKAGE CURRENT OF BIOMETRIC INFORMATION MEASUREMENT DEVICE

(71) Applicant: I-SENS, INC., Seoul (KR)

(72) Inventors: Young Jae Kang, Seoul (KR); Jung Uk Ha, Seoul (KR); Jin Won Lee, Seoul (KR)

(73) Assignee: I-SENS, INC., Seoul (KR)

( * ) Notice: Subject to any disclaimer, the term of this patent is extended or adjusted under 35 U.S.C. 154(b) by 776 days.

(21) Appl. No.: 18/265,161

(22) PCT Filed: Jul. 28, 2021

(86) PCT No.: PCT/KR2021/009799
§ 371 (c)(1),
(2) Date: Jun. 2, 2023

(87) PCT Pub. No.: WO2022/131473
PCT Pub. Date: Jun. 23, 2022

(65) Prior Publication Data

US 2024/0019500 A1 Jan. 18, 2024

(30) Foreign Application Priority Data

Dec. 14, 2020 (KR) ........................ 10-2020-0174278

(51) Int. Cl.
*G01R 31/52* (2020.01)
*A61B 5/145* (2006.01)
(Continued)

(52) U.S. Cl.
CPC .......... *G01R 31/52* (2020.01); *A61B 5/14503* (2013.01); *A61B 5/14532* (2013.01); *A61B 5/1495* (2013.01); *G08B 21/182* (2013.01)

(58) Field of Classification Search
None
See application file for complete search history.

(56) References Cited

U.S. PATENT DOCUMENTS

2006/0247508 A1 11/2006 Fennell
2019/0175082 A1* 6/2019 Varsavsky ............ A61B 5/4839

FOREIGN PATENT DOCUMENTS

KR 10-1093171 12/2011
KR 10-2017-0058828 5/2017
(Continued)

OTHER PUBLICATIONS

Eisner et al. Leakage Current Standards Simplified; https://www.mddionline.com/components/leakage-current-standards-simplified; 2004 (Year: 2004).*
(Continued)

*Primary Examiner* — Jay B Shah
(74) *Attorney, Agent, or Firm* — WOMBLE BOND DICKINSON (US) LLP

(57) ABSTRACT

The present invention relates to a method for detecting a leakage current during use of a biometric data measuring device, and more particularly, a method is provided whereby it is possible to detect whether there is a leakage in a current applied to a sensor in a state of measuring biometric data while a part of the sensor is inserted into the user's skin, by comparing the difference in magnitude between an applied current applied via one terminal of the sensor, which is comprised in the biometric data measuring device, and an output current output via the other terminal of the sensor.

10 Claims, 5 Drawing Sheets

(51) Int. Cl.
*A61B 5/1495* (2006.01)
*G08B 21/18* (2006.01)

(56) References Cited

FOREIGN PATENT DOCUMENTS

| | | |
|---|---|---|
| KR | 10-1878449 | 7/2018 |
| KR | 10-2020-0036121 | 4/2020 |
| KR | 10-2020-0097270 | 8/2020 |
| WO | 2019/118060 | 6/2019 |

OTHER PUBLICATIONS

Tan et al. A highly sensitive wide-range weak current detection circuit for implantable glucose monitoring; IEICE Electronics Express, vol. 13, No. 8, 1-10 (Year: 2016).*

Extended European Search Report dated Aug. 13, 2024 for European Patent Application No. 21906778.2.

Withana Anusha wdanusha@gmail gom et al: "Tacttoo a Thin and Feel-Through Tattoo for On-Skin Tactile Output", Proceedings of the 2018 ACM International Conference on Interactive Surfaces and Spaces, ACM, New York, NY, USA, Oct. 11, 2018, pp. 365-378, XP058545146.

Notice of Allowance dated Sep. 22, 2022 for Korean Patent Application No. 10-2020-0174278 and its English translation provided by Applicant's foreign counsel.

International Search Report for PCT/KR2021/009799 mailed on Nov. 3, 2021 and its English translation from WIPO (now published as WO 2022/131473).

Written Opinion of the International Searching Authority for PCT/KR2021/009799 mailed on Nov. 3, 2021 and its English translation from WIPO (now published as WO 2022/131473).

* cited by examiner

[FIG.1]
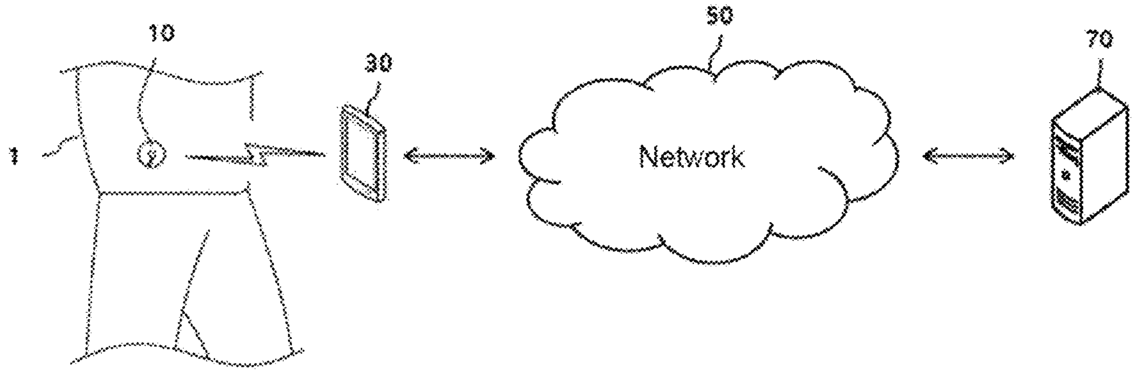
[FIG.2]
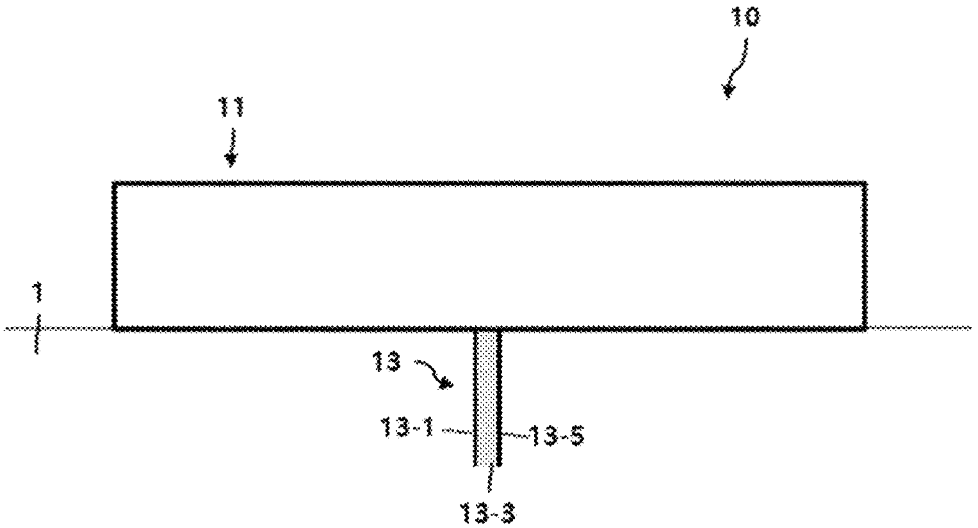
[FIG.3]
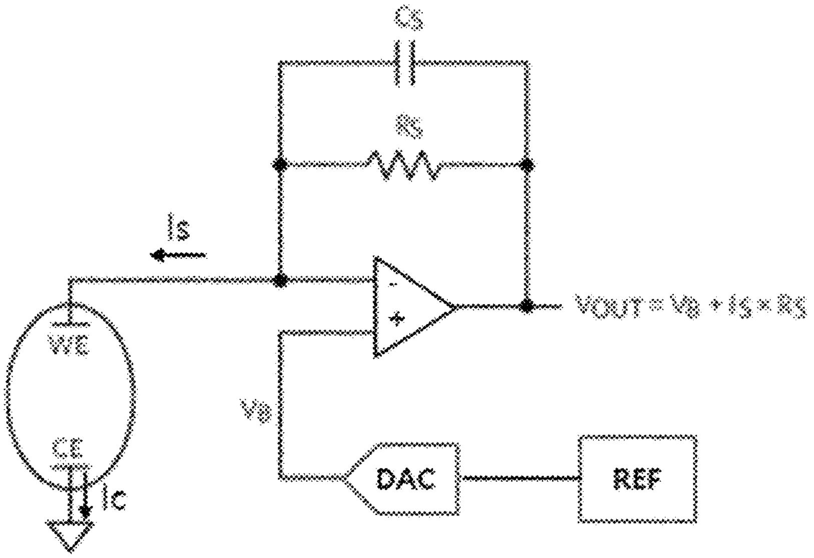

[FIG.4]
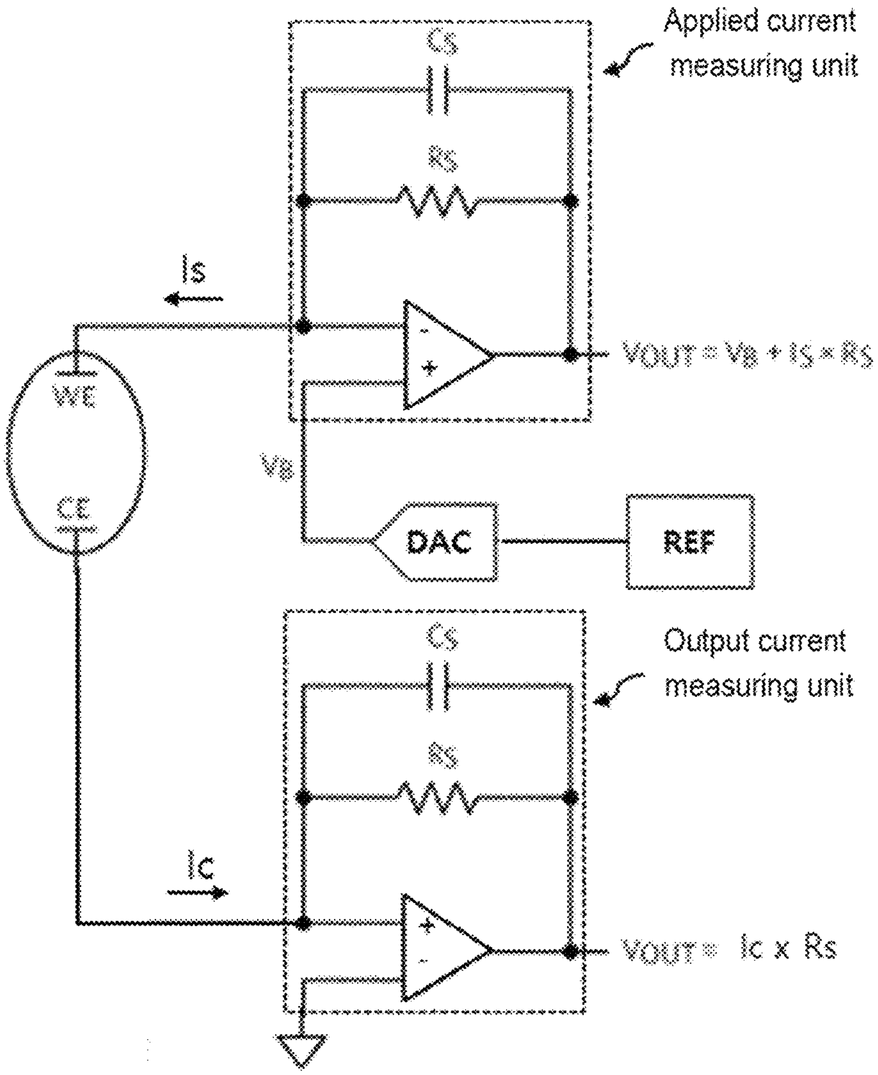

[FIG.5]
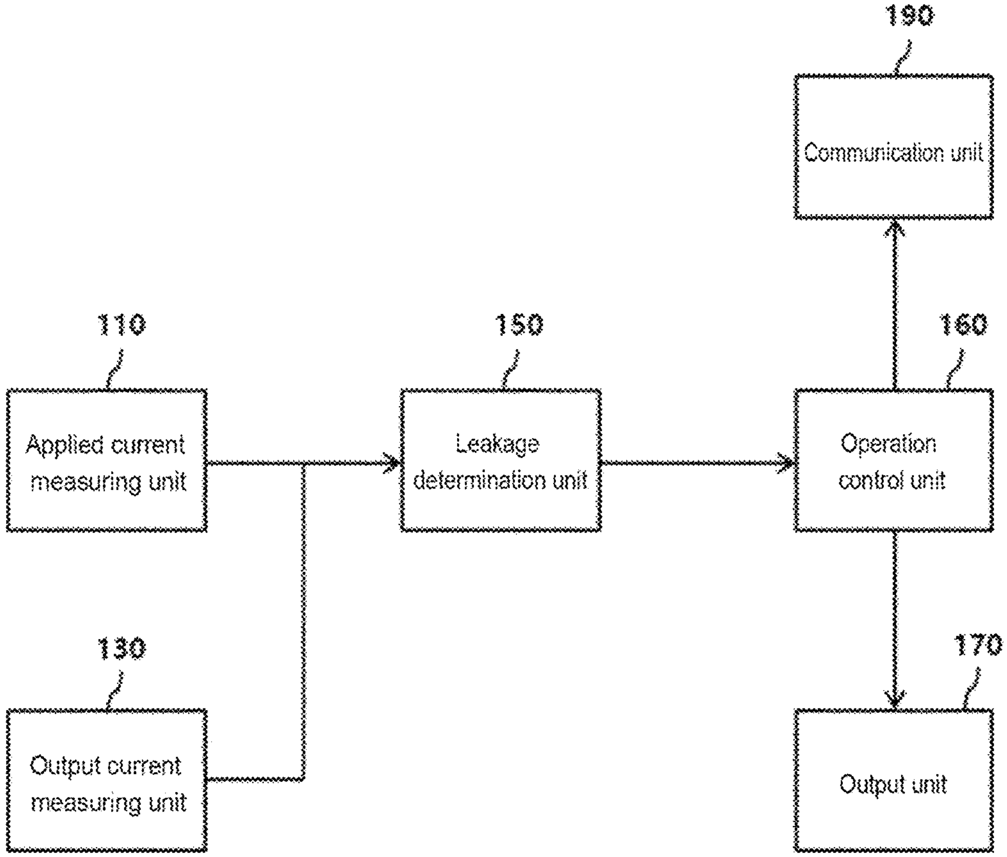

[FIG.6]
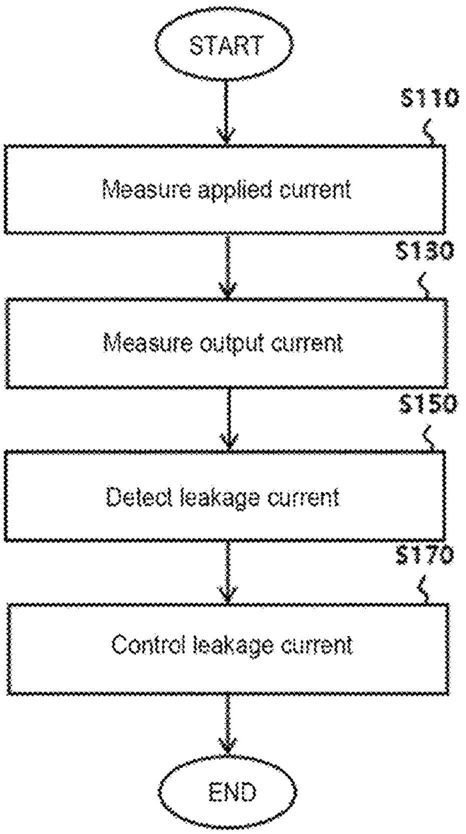
[FIG.7]
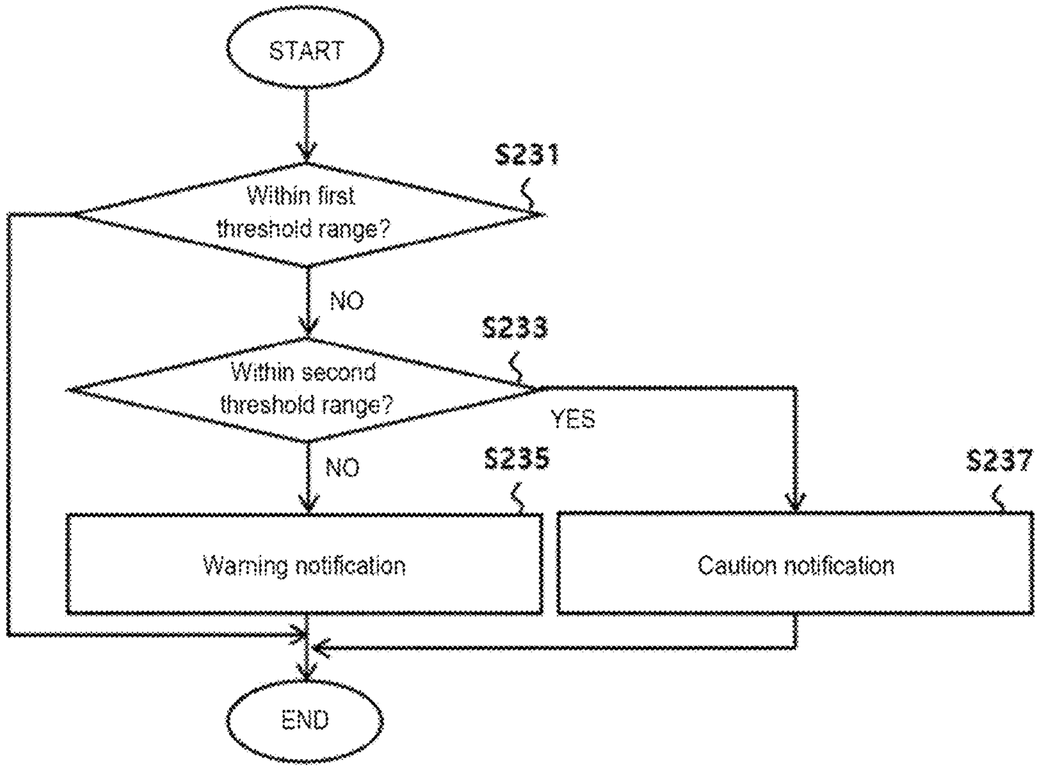

[FIG.8]
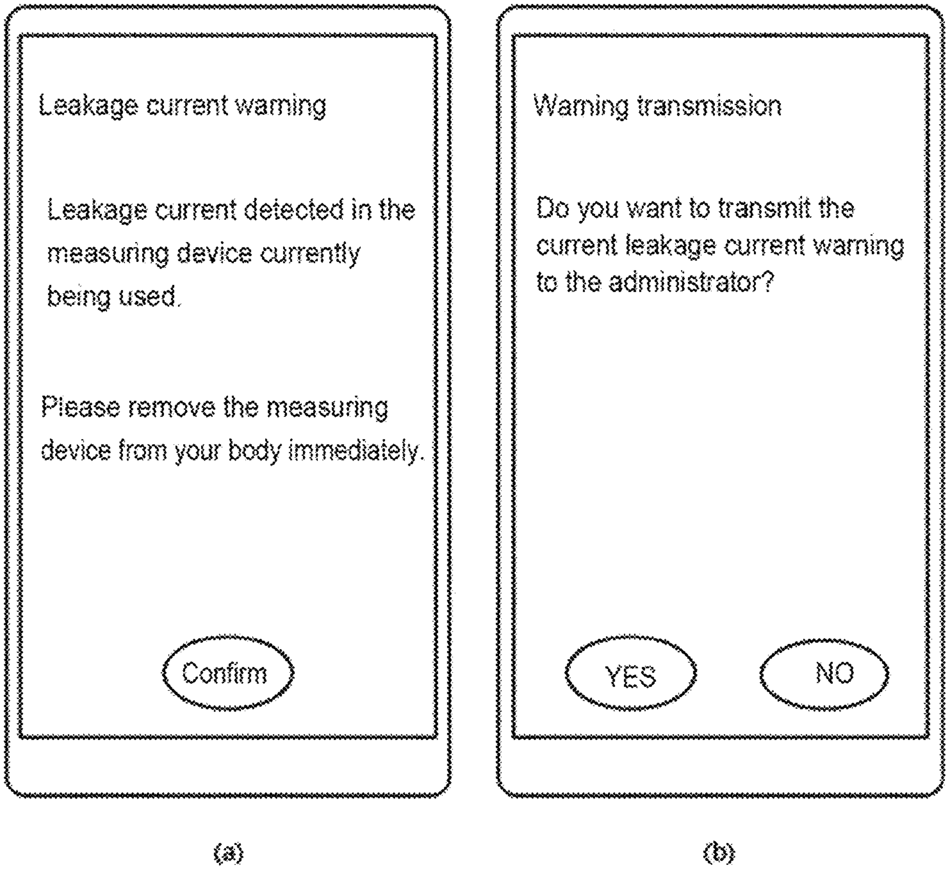

METHOD FOR DETECTING LEAKAGE CURRENT OF BIOMETRIC INFORMATION MEASUREMENT DEVICE

CROSS-REFERENCE TO RELATED APPLICATIONS

The present application is the U.S. National Phase of PCT Application No. PCT/KR2021/009799 filed on Jul. 28, 2021, which claims the priority to Korean Patent Application No. 10-2020-0174278 filed on Dec. 14, 2020, the entire contents of which are incorporated herein by reference.

TECHNICAL FIELD

The present invention relates to a method for detecting a leakage current during measurement of biometric data by using a biometric data measuring device, and more particularly, a method is provided whereby it is possible to detect whether there is leakage of current in a sensor in the state of measuring biometric data while a part of a sensor is inserted into the user's skin, by comparing the difference in magnitudes between an applied current applied via one terminal of the sensor inserted into the skin and an output current output via the other terminal of the sensor.

BACKGROUND

Diabetes is a leading cause of death worldwide and is a factor which causes physical impairments, and therefore many people develop health problems due to diabetes. In particular, diabetes is a serious disease which causes heart and kidney disease, blindness, neural damage and high blood pressure. Looking at long-term clinical studies, the occurrence of complications can be significantly reduced by means of adequately controlling blood glucose levels. Therefore, it is important to continuously manage diabetes, and a major factor thereof is self-monitoring of blood glucose levels.

Due to such requirements, personal biometric devices which can directly test the blood glucose of the user are widely supplied to and used by users. Typical blood glucose measuring devices measure a user's blood glucose level by smearing the user's blood onto a sensor strip in the form of a test paper. That is, the sensor strip smeared with blood is inserted into the blood glucose measuring device and the blood glucose level measured via the sensor strip is displayed on the blood glucose measuring device.

At this time, the blood glucose measuring device receives an electrical signal generated by an electrochemical reaction of the collected blood and the reactants inside the sensor strip and so measures the blood glucose level. This blood-collecting blood glucose meter (finger prick method) helps with a diabetes patient's blood glucose management, but there is a problem in that it is difficult to accurately understand the frequently changing blood glucose value since only the result at the time of measurement is indicated.

Diabetes patients generally move between hyperglycaemic and hypoglycaemic states, with emergencies occurring in the hypoglycaemic state, and, when the supply of glucose does not last for a long time, they may lose consciousness or, in the worst case, may lose their lives. Therefore, the prompt detection of a hypoglycaemic state is very important to diabetes patients. But blood-collecting blood glucose meters which intermittently measure blood glucose have obvious limitations.

In order to overcome the limitations of such blood-collecting blood glucose meters, a continuous blood glucose measuring system (Continuous Glucose Monitoring System, CGMS) which is inserted into the body to measure blood glucose at intervals of a few minutes has been developed, and this can be used to manage diabetic patients and easily cope with emergency situations.

The continuous blood glucose measuring system comprises: a measuring device which is inserted into the human body and is for collecting test material such as a bodily fluid of the user and measuring the blood glucose; and a receiver for communicating with the measuring device and displaying the blood glucose data measured by the measuring device. Meanwhile, measuring devices typically consist of a sensor and a transmitter, and when the measuring device is attached to the skin, a portion of the sensor that is inserted into the skin measures the blood glucose and provides the measured blood glucose data to the transmitter.

Measuring devices have a fixed term of life, for example, a service life of 15 days or 1 month, and are attached to the user's body during the service life to continuously measure the user's blood glucose data and transmit the measured blood glucose data to the receiver periodically or upon request from the receiver.

The receiver not only outputs the blood glucose data received from the measuring device to the user, but also can provide an alarm to the user when the user has hyperglycaemia or hypoglycaemia on the basis of the blood glucose data, or can monitor the service condition of the measuring device and provide an alarm to the user.

Biometric data measuring devices as described above are products that are used by attaching to the user's skin, and undergo multiple safety tests in advance in the manufacturing process before being provided to the user. Among the safety tests, there is a test for whether there is a leakage current in the measuring device. This test for leakage current is a test for the occurrence of a leakage current from the measuring device itself.

However, despite the measuring device being one that has undergone testing relating to whether there is a leakage current in the manufacturing process before being provided to the user, when the measuring device is actually attached to the user's skin during use, it is difficult to determine whether there is a leakage current in the sensor partially inserted into the skin. That is, in the manufacturing process, it is difficult to determine if there is a leakage current in the sensor inserted into the skin during use of the measuring device, and so a problem is caused in that, when there is a leakage current during use of the measuring device, there is danger to the user or accurate blood glucose measurement is difficult.

DETAILS OF THE INVENTION

Problem to be Solved

The present invention aims to resolve the problems of the conventional biometric data measuring device mentioned above, and an object of the present invention is to provide a method for detecting whether there is a leakage current in the sensor in the state of measuring biometric data by inserting into the user's skin a part of the sensor, which is comprised in the biometric data measuring device.

Another object of the present invention is to provide a method for detecting a leakage current, whereby it is possible to notify the user of the leakage current state by differentiating between leakage current and noise generated during use while the biometric data measuring device is attached to the user's body.

Yet another object of the present invention is to provide a method for detecting a leakage current, and which helps the user measure the biometric data safely and accurately by providing data relating to the leakage current state to not only the user terminal but also the manufacturer, when there is a leakage current in the sensor inserted into the skin during use of the biometric data measuring device.

Solution to the Problem

In order to achieve the objects of the present invention, a method for detecting whether there is a leakage current in the sensor inserted into the skin during use of a measuring device according to the present invention is characterized in that the method comprises steps of: measuring the magnitude of an applied current which is applied from a transmitter to one electrode of the sensor; measuring the magnitude of an output current which is output from the other electrode of the sensor; and determining whether there is leakage current in the sensor, on the basis of the magnitude of the applied current and the magnitude of the output current.

The method for detecting a leakage current according to the present invention is characterized in that the one electrode of the sensor and the other electrode of the sensor are inserted into the skin when the measuring device is attached to a user's skin to measure the user's biometric data; and an applied current is applied via the one electrode of the sensor inserted into the skin and an output current is output from the other electrode of the sensor inserted into the skin.

Here, the present invention is characterized in that the one electrode and the other electrode of the sensor are insulated from each other; and the one electrode of the sensor operates as a working electrode and the other electrode of the sensor operates as a counter electrode.

The method for detecting a leakage current according to the present invention is characterized in that, if the magnitude of the applied current and the magnitude of the output current are the same as each other, it is determined that there is no leakage current in the sensor.

Preferably, a characterizing feature according to one embodiment of the present invention is that the step of determining whether there is a leakage current further comprises steps of: determining whether the difference in magnitudes of the applied current and the output current exceeds a first threshold range; and determining whether the difference in magnitude between the applied current and the output current exceeds a second threshold range, wherein the second threshold range is larger than the first threshold range.

A characterizing feature according to one embodiment of the present invention is that, in the step of determining whether there is a leakage current, if the difference between the applied current and the output current is within the first threshold range, the applied current and the output current are determined to be the same as each other and so the leakage current state is determined to be a normal state.

A characterizing feature according to one embodiment of the present invention is that, in the step of determining whether there is a leakage current, if the difference between the applied current and the output current is larger than the first threshold range and is smaller than the second threshold range, the leakage current state is determined to be a caution state.

A characterizing feature according to one embodiment of the present invention is that, in the step of determining whether there is a leakage current, if the difference between the applied current and the output current exceeds the second threshold range, the leakage current state is determined to be a warning state.

Preferably, the method for detecting a leakage current according to the present invention is characterized in that the method further comprises a step of outputting the leakage current state.

Preferably, the method for detecting a leakage current according to the present invention is characterized in that the method further comprises a step of generating a notification message for notifying the leakage current state, and transmitting the notification message to a user terminal.

The method for detecting a leakage current according to the present invention is characterized in that the notification message is transmitted to a management server through the user terminal.

Advantages of the Invention

The method for detecting whether there is a leakage current in the sensor inserted into the skin in a biometric data measuring device according to the present invention has the advantages such as the following.

Firstly, the leakage current measuring method according to the present invention makes it possible to detect whether there is a leakage current in a sensor in the state of measuring biometric data while a part of a sensor is inserted into the user's skin, by comparing the difference in magnitude between an applied current applied via one terminal of the sensor, which is comprised in the biometric data measuring device, and an output current output via the other terminal of the sensor.

Secondly, the method for detecting a leakage current according to the present invention makes it possible to notify the user of the leakage current state by differentiating between leakage current and noise generated in the sensor during use while the biometric data measuring device is attached to the user's body, by calculating the difference in magnitude between an applied current applied via one terminal of the sensor, and an output current output via the other terminal of the sensor and comparing the magnitude difference to a first threshold range or a second threshold range.

Thirdly, the method for detecting a leakage current according to the present invention makes it possible for the user to measure the biometric data safely and accurately by providing data relating to the leakage current state to not only the user terminal but also the manufacturer, when there is a leakage current in the sensor inserted into the skin during use of the biometric data measuring device.

BRIEF DESCRIPTION OF THE DRAWINGS

FIG. 1 is a schematic diagram depicting a continuous blood glucose data measuring system according to one embodiment of the present invention.

FIG. 2 depicts an example of a measuring device (10) fitted to a body.

FIG. 3 is a drawing for describing a circuit for measuring blood glucose values in the measuring device.

FIG. 4 depicts a functional block diagram of a device for detecting whether there is leakage of current flowing between the working electrode and counter electrode of a sensor inserted into the skin in accordance with the present invention.

FIG. 5 depicts an example of a leakage current detection circuit according to the present invention.

FIG. 6 is a flow diagram for describing the leakage current detection method according to the present invention.

FIG. 7 is a flow diagram for describing an example of a step of detecting a leakage current in the present invention.

FIG. 8 depicts an example of a warning notification message transmitted to a user terminal.

SPECIFIC DETAILS FOR IMPLEMENTING THE INVENTION

It should be noted that the technical terms used in the present invention are merely used to describe a specific embodiment of the invention, and are not intended to limit the present invention. Furthermore, the technical terms used in the present invention should be interpreted as having the meaning commonly understood by a person skilled in the art to which the present invention belongs unless specifically defined otherwise in the present invention, and should not be interpreted as having an excessively inclusive meaning or an excessively limited meaning. Furthermore, when a technical term used in the present invention is an erroneous technical term that fails to accurately express a concept of the present invention, it should be understood as having been replaced by a technical term that can be correctly understood by those skilled in the art.

Furthermore, expressions in the singular used in the present invention include expressions in the plural unless clearly intended otherwise in context. In the present invention, terms such as "consisting of" or "comprising" should not necessarily be interpreted as including all the constituent elements or steps described in the invention, and some constituent elements or some steps may not be included, or additional constituent elements or steps may be further included.

Furthermore, it should be noted that the accompanying drawings are merely to facilitate the understanding of the concept of the present invention, and the concept of the present invention should not be construed as being limited by the accompanying drawings.

Hereinbelow, the method for detecting a leakage current of a biometric data measuring device according to the present invention is described with reference to the accompanying drawings.

Hereinbelow, blood glucose data is described as an example of biometric data, but the measuring device can measure various pieces of biometric data in accordance with the field that the present invention is applied to, and these are within the scope of the present invention.

FIG. 1 is a schematic diagram depicting a continuous blood glucose data measuring system according to one embodiment of the present invention.

Referring to FIG. 1, a measuring device (10) is attached to the body and the measuring device (10) periodically extracts a bodily fluid of the body to measure blood glucose. The measuring device (10) is provided with a sensor, one end of which is inserted into the skin when attached to the body; and a transmitter which processes the blood glucose data measured by the sensor. The transmitter uses calibration data to calibrate the blood glucose data measured via the sensor, and either stores the calibrated blood glucose data or transmits same to a communication terminal.

A communication terminal (30) is a terminal capable of receiving blood glucose data from the measuring device (10) and displaying the received blood glucose data to a user, and a mobile terminal capable of communicating with the measuring device (10) such as a smartphone, tablet PC, or notebook can be used. Naturally, the communication terminal (30) is not limited thereto, and the type of terminal does not matter as long as the terminal includes a communication function and a program or application can be installed.

The measuring device (10) transmits the measured blood glucose data to the communication terminal (30) periodically at set times or upon request by the communication terminal (30), and the measuring device (10) and the communication terminal (30) can establish communication between each other in a wired fashion by means of a USB cable or the like or can establish communication via a wireless communication method such as infra-red communication, NFC communication, or Bluetooth.

Meanwhile, the communication terminal (30) can transmit the blood glucose data received from the measuring device (10) to a management server (70) via a network (50) in real-time or upon request, or can monitor the operating state of the measuring device (10) and transmit the monitoring results for the measuring device (10) to the management server (70) via the network (50).

Here, the measuring device (10) is attached to a part of the body by means of an applicator (not depicted), and the applicator has the measuring device (10) provided therein and is operated through user manipulation to discharge the measuring device (10) to the outside and attach same to a specific body region of the user.

When the measuring device (10) is attached to part of the body using the applicator, in order to insert one end of the sensor provided in the measuring device (10) into the skin, the applicator is provided with: a needle (not depicted) which is formed surrounding on the inside thereof the one end of the sensor; a first resilient member (not depicted) which pushes the needle and one end of the sensor into the skin together; and a second resilient member (not depicted) for withdrawing only the needle.

FIG. 2 depicts an example of a measuring device (10) fitted to the body.

Referring to FIG. 2, the measuring device (10) is attached to the body using the applicator, and the housing of a transmitter (11) is attached to the body surface while a part of a sensor (13) is disposed inserted in the skin (1).

On the one end of the sensor (13), a working electrode (13-1) and a counter electrode (13-5) are formed with an insulation layer (13-3) placed in between, and, on the other end of the sensor (13), a working electrode terminal (not depicted) which is connected to the working electrode and a counter electrode terminal (not depicted) which is connected to the counter electrode are formed. Here, the working electrode terminal and the counter electrode terminal are connected to the transmitter (11).

When a fixed voltage is applied to the working electrode (13-1) and the counter electrode (13-5) through the transmitter (11), enzymes dispersed in the working electrode and the glucose in the bodily fluid chemically react with each other and produce electrons and thus a current flows between the working electrode (13-1) and the counter electrode (13-5). The transmitter (11) measures user's blood glucose value from the magnitude of the current flowing between the working electrode (13-1) and the counter electrode (13-5).

FIG. 3 is a drawing for describing a circuit for measuring blood glucose values in the measuring device, and referring to FIG. 3, when power is applied to the measuring device, after the measuring device has been attached to the body, a fixed voltage is applied between the working electrode (WE) and the counter electrode (CE) of the sensor inserted into the skin, and electrons produced through the oxidation of the glucose in the bodily fluid by the enzymes are delivered to the working electrode. Thus, a current is made to flow from the working electrode to the counter electrode and the user's blood glucose value is measured from the magnitude of the current flowing at this time.

Therefore, when the working electrode and the counter electrode of the sensor are inserted into the skin to measure the blood glucose value, the magnitude of the applied current ($I_s$) applied to the working electrode of the sensor and the magnitude of the output current (I c) output from the counter electrode are the same as each other.

However, if the insulation of the transmitter breaks down or damage occurs to the working electrode or counter electrode during use with the measuring device disposed on the body, the current flowing between the working electrode and the counter electrode of the sensor inserted into the skin may leak, and, in such cases, the magnitude of the applied current applied to the working electrode and the magnitude of the output current output from the counter electrode are different from each other.

FIG. 4 depicts a functional block diagram of a device for detecting whether there is leakage of the current flowing between the working electrode and counter electrode of the sensor inserted into the skin in accordance with the present invention.

More specifically, referring to FIG. 4, an applied current measuring unit (110) measures the magnitude of the applied current applied to the working electrode inserted into the skin, and an output current measuring unit (130) measures the magnitude of the output current output from the counter electrode inserted into the skin.

A leakage determination unit (150) calculates the difference in magnitude between the applied current and output current which were measured at the same time, and from the difference in magnitude between the applied current and output current, determines whether the current flowing between the working electrode and the counter electrode is leaking.

Depending on whether there is a leakage of the current flowing between the working electrode and the counter electrode, an operation control unit (160) can, if there is a leakage current, generate a notification message for notification of the leakage current and transmit same to the user terminal via a communication unit (190) or can notify the user that there is a leakage current via an output unit (170).

Here, the output unit (170) is disposed inside or outside of the measuring device and is the means for notifying the user that there is a leakage current, and, for example, a speaker, vibrator or warning light may be used.

When the user receives the notification message or a notification signal is output via the output unit (170), an incident which could be caused by the leakage current can be prevented by removing the measuring device attached to the user's body. Furthermore, a new measuring device can be attached to the body to accurately measure the user's blood glucose value.

FIG. 5 depicts an example of a leakage current detection circuit according to the present invention.

FIG. 6 is a flow diagram for describing the leakage current detection method according to the present invention.

More specifically referring to FIG. 6, the magnitude of the applied current applied to the working electrode of the sensor and the magnitude of the output current output from the counter electrode of the sensor are measured at the same time (S110, 130).

The difference in magnitude between the applied current and output current which were measured at the same time is calculated to detect whether current flowing between the working electrode and counter electrode is leaking (S150).

The leakage current is controlled in accordance with whether there is leakage in the current flowing between the working electrode and counter electrode (S170).

As an example of controlling the leakage current, control is enacted to interrupt the power applied to the working electrode or the counter electrode from a battery of the transmitter when the current flowing between the working electrode and counter electrode is leaking. Thus, no voltage is applied between the working electrode and the counter electrode.

As another example of controlling the leakage current, a notification message notifying that a leakage current has been detected is generated and the generated notification message is transmitted to a user terminal, when the current flowing between the working electrode and counter electrode is leaking. The user can remove the measuring device attached to the user's body on the basis of the notification message.

As yet another example of controlling the leakage current, a notification signal is output via the output unit when the current flowing between the working electrode and counter electrode is leaking. Here, the notification signal is a signal for notifying that a leakage current has been detected, and is output via a speaker, warning light or vibrator depending on the kind of notification signal.

FIG. 7 is a flow diagram for describing an example of the step of detecting a leakage current in the present invention.

More specifically referring to FIG. 7, the magnitude of the applied current applied to the working electrode and the magnitude of the output current output from the counter electrode are measured at the same time and it is determined whether the difference in magnitude between the applied current and the output current is within a first threshold range (S231).

If there is no difference in magnitude between the applied current and the output current or the difference is within the first threshold range, it is determined that there is no leakage current.

However, if the difference in magnitude between the applied current and the output current exceeds the first threshold range, it is determined whether the difference in magnitude between the applied current and the output current exceeds a second threshold range (S233). Here, the second threshold range is characterized in that it is larger than the first threshold range.

If the difference in magnitude between the applied current and the output current is between the first threshold range and the second threshold range, a caution notification message is generated and transmitted to the user terminal or a caution notification signal is generated and output via the output unit (S237).

However, if the difference in magnitude between the applied current and the output current exceeds the second threshold range, a warning notification message is generated and transmitted to the user terminal or a warning notification signal is generated and output via the output unit (S235).

That is, if the difference in magnitude between the applied current and the output current is between the first threshold range and the second threshold range, this difference can be determined to be noise temporarily generated by stress applied to the sensor due to the user's movement or it can be determined that the leakage level of the current flowing between the working electrode and counter electrode is not large. In such a case, a caution notification message or caution notification signal is simply provided to the user so that the user can determine for themselves whether there is a leakage current or the magnitude thereof.

Meanwhile, if the difference in magnitude between the applied current and the output current exceeds the second threshold range, it can be determined that a substantial portion of the current flowing between the working electrode and the counter electrode is leaking. In such a case, a warning notification message or warning signal is provided to the user so that the user can act promptly to remove the measuring device.

FIG. 8 depicts an example of a warning notification message transmitted to the user terminal.

Referring to FIG. 8(*a*), the warning notification message is displayed on the user terminal and the user can remove the measuring device promptly on the basis of the warning notification message.

Referring to FIG. 8(*b*), the user can transmit a leakage current warning report to the management server when a leakage current warning is given. When transmitting the leakage current warning report to the management server, the user terminal can generate a leakage current warning report message comprising data such as the difference in magnitude between the applied current and output current, a measuring device identifier, and time that the leakage current was detected, and transmit same to the management server.

Meanwhile, the embodiments of the present invention described above may be written as a computer-executable program and may be implemented in a general-purpose digital computer that operates the program using a computer-readable recording medium.

Computer-readable recording media include storage media such as magnetic storage media (e.g., ROM, floppy disk, hard disk, etc.), optical reading media (e.g., CD-ROM, DVD, etc.), and carrier waves (e.g., transmission over the Internet).

The present invention has been described with reference to the embodiments depicted in the drawings, but the embodiments are merely examples, and it should be understood by those skilled in the art that various modifications and other equivalent embodiments are possible. Therefore, the true technical scope of protection for the present invention should be determined by the technical concepts in the accompanying registered claims.

What is claimed is:

1. A method for detecting, in a measuring device comprising a sensor comprising a working electrode and a counter electrode, and a transmitter, whether there is a leakage current in the sensor which is inserted into a user's skin, characterized in that, the method for detecting the leakage current comprises steps of:

measuring the magnitude of an applied current which is applied from the transmitter to the working electrode of the sensor;

measuring the magnitude of an output current which is output from the counter electrode of the sensor; and determining a leakage current state of the sensor inserted into the user's skin by comparing a difference in magnitude between the applied current and the output current with a first threshold range and a second threshold range, wherein the second threshold range is larger than the first threshold range.

2. The method for detecting the leakage current as claimed in claim 1, characterized in that the working electrode of the sensor and the counter electrode of the sensor are inserted into the user's skin when the measuring device is attached to the user's skin to measure the user's biometric data; and the applied current is applied via the working electrode of the sensor inserted into the user's skin and the output current is output from the counter electrode of the sensor inserted into the user's skin.

3. The method for detecting the leakage current as claimed in claim 2, characterized in that the working electrode and the counter electrode of the sensor are insulated from each other.

4. The method for detecting the leakage current as claimed in claim 3, characterized in that if the magnitude of the applied current and the magnitude of the output current are the same as each other, it is determined that the applied current is not leaking to the body through the sensor.

5. The method for detecting the leakage current as claimed in claim 1, characterized in that, in the step of determining the leakage current state, if the difference between the applied current and the output current is within the first threshold range, the applied current and the output current are determined to be the same as each other and so the leakage current state is determined to be a normal state.

6. The method for detecting the leakage current as claimed in claim 5, characterized in that the method further comprises a step of:

outputting the leakage current state.

7. The method for detecting the leakage current as claimed in claim 5, characterized in that the method further comprises a step of:

generating a notification message for notifying the leakage current state, and transmitting the notification message to a user terminal.

8. The method for detecting the leakage current as claimed in claim 7, characterized in that the notification message is transmitted to a management server through the user terminal.

9. The method for detecting the leakage current as claimed in claim 1, characterized in that, in the step of determining the leakage current state, if the difference between the applied current and the output current is larger than the first threshold range and is smaller than the second threshold range, the leakage current state is determined to be a caution state.

10. The method for detecting the leakage current as claimed in claim 1, characterized in that, in the step of determining the leakage current state, if the difference between the applied current and the output current exceeds the second threshold range, the leakage current state is determined to be a warning state.

* * * * *